United States Patent
Freeman et al.

(10) Patent No.: US 11,173,265 B2
(45) Date of Patent: *Nov. 16, 2021

(54) VENTILATION MONITORING

(71) Applicant: ZOLL Medical Corporation, Chelmsford, MA (US)

(72) Inventors: Gary A. Freeman, Waltham, MA (US); Guy R. Johnson, Wilton, NH (US); Annemarie Silver, Bedford, MA (US)

(73) Assignee: ZOLL Medical Corporation, Chelmsford, MA (US)

( * ) Notice: Subject to any disclaimer, the term of this patent is extended or adjusted under 35 U.S.C. 154(b) by 403 days.

This patent is subject to a terminal disclaimer.

(21) Appl. No.: 16/242,385

(22) Filed: Jan. 8, 2019

(65) Prior Publication Data

US 2019/0175852 A1    Jun. 13, 2019

Related U.S. Application Data

(63) Continuation of application No. 14/109,519, filed on Dec. 17, 2013, now Pat. No. 10,220,169.

(Continued)

(51) Int. Cl.
*A61M 16/04*    (2006.01)
*A61B 5/087*    (2006.01)
(Continued)

(52) U.S. Cl.
CPC ......... *A61M 16/0411* (2014.02); *A61B 5/087* (2013.01); *A61B 5/0809* (2013.01);
(Continued)

(58) Field of Classification Search
CPC .................. A61B 5/0836; A61M 2016/0413
See application file for complete search history.

(56) References Cited

U.S. PATENT DOCUMENTS

| 4,879,999 A | 11/1989 | Leiman et al. |
| 4,951,678 A | 8/1990 | Joseph et al. |

(Continued)

OTHER PUBLICATIONS

Li, "Capnography Alone is Imperfect for Endotracheal Tube Placement Confirmation During Emergency Intubation", The Journal of Emergency Medicine, 2001, pp. 223-229, vol. 20:3.

*Primary Examiner* — Meredith Weare
(74) *Attorney, Agent, or Firm* — The Webb Law Firm (57) ABSTRACT

A ventilation monitoring system for assisting in proper placement of an endotracheal tube in a subject includes: a capnography sensor configured to be placed in fluid communication with the endotracheal tube and to provide information representative of the subject's breath; and a processor in communication with the capnography sensor. The processor is configured to provide an indication of proper endotracheal tube placement when (1) a first indication of the subject's breath and a positive result of a first auscultation are identified within a first predetermined time period, and (2) a second indication of the subject's breath and a positive result of a second auscultation are identified within a second predetermined time period. The first auscultation includes auscultation of a subject's left lung, right lung, left axillary region, right axillary region, or abdomen. The second auscultation includes auscultation of another region of the subject different from the first auscultation.

32 Claims, 8 Drawing Sheets

Related U.S. Application Data (60) Provisional application No. 61/740,789, filed on Dec. 21, 2012.

(51) Int. Cl.

| | |
|---|---|
| *A61B 7/00* | (2006.01) |
| *A61M 16/00* | (2006.01) |
| *A61N 1/39* | (2006.01) |
| *A61N 1/04* | (2006.01) |
| *A61B 5/08* | (2006.01) |
| *A61B 5/083* | (2006.01) |
| *A61M 16/10* | (2006.01) |
| *A61B 5/318* | (2021.01) |

(52) U.S. Cl.
CPC ............ *A61B 5/0836* (2013.01); *A61B 7/003* (2013.01); *A61M 16/0051* (2013.01); *A61M 16/021* (2017.08); *A61N 1/046* (2013.01); *A61N 1/3925* (2013.01); *A61B 5/318* (2021.01); *A61M 16/0084* (2014.02); *A61M 2016/0413* (2013.01); *A61M 2016/103* (2013.01); *A61M 2205/054* (2013.01); *A61M 2205/332* (2013.01); *A61M 2205/3375* (2013.01); *A61M 2205/3553* (2013.01); *A61M 2205/3561* (2013.01); *A61M 2205/3569* (2013.01); *A61M 2205/3584* (2013.01); *A61M 2205/3592* (2013.01); *A61M 2205/505* (2013.01); *A61M 2205/581* (2013.01); *A61M 2205/60* (2013.01); *A61M 2205/8206* (2013.01); *A61M 2230/04* (2013.01); *A61M 2230/42* (2013.01); *A61M 2230/432* (2013.01); *A61M 2230/65* (2013.01)

(56) References Cited

U.S. PATENT DOCUMENTS

| | | |
|---|---|---|
| 6,168,568 B1 | 1/2001 | Gavriely |
| 6,224,549 B1 | 5/2001 | Drongelen |
| 6,616,597 B2 | 9/2003 | Schock et al. |
| 6,929,600 B2 | 8/2005 | Hill |
| 8,038,629 B2 | 10/2011 | Solanki et al. |
| 8,147,419 B2 | 4/2012 | Krauss et al. |
| 8,394,031 B2 | 3/2013 | Mansy et al. |
| 8,416,291 B2 | 4/2013 | Carrey et al. |
| 10,220,169 B2 * | 3/2019 | Freeman ................ A61N 1/046 |
| 2002/0072647 A1 | 6/2002 | Schock et al. |
| 2003/0018276 A1 | 1/2003 | Mansy et al. |
| 2003/0078476 A1 | 4/2003 | Hill |
| 2004/0236240 A1 | 11/2004 | Kraus et al. |
| 2008/0251070 A1 | 10/2008 | Pinskiy et al. |
| 2009/0099479 A1 | 4/2009 | Solanki et al. |
| 2009/0322867 A1 | 12/2009 | Carrey et al. |
| 2011/0166442 A1 | 7/2011 | Sarvazyan |
| 2011/0224568 A1 | 9/2011 | Wik |
| 2011/0245704 A1 | 10/2011 | Monsieurs et al. |
| 2012/0065469 A1 | 3/2012 | Allyn et al. |
| 2012/0116156 A1 | 5/2012 | Lederman |
| 2012/0123219 A1 | 5/2012 | Georgiev et al. |
| 2012/0302910 A1 | 11/2012 | Freeman et al. |
| 2013/0098363 A1 | 4/2013 | Forte et al. |
| 2013/0158452 A1 | 6/2013 | Juto et al. |
| 2014/0058253 A1 | 2/2014 | Prough et al. |

\* cited by examiner

VENTILATION MONITORING

CLAIM OF PRIORITY

This application is a continuation of U.S. patent application Ser. No. 14/109,519, filed Dec. 17, 2013, which claims priority under 35 U.S.C. § 119(e) to U.S. Patent Provisional Application No. 61/740,789, filed on Dec. 21, 2012, the entire contents of each of which are hereby incorporated by reference.

TECHNICAL FIELD

The invention relates generally to methods and associated equipment for monitoring ventilation.

BACKGROUND

A tracheal tube is a catheter that is inserted into the trachea to establish and maintain a subject's airway. Tracheal tubes are frequently used for airway management in settings of general anesthesia, critical care, mechanical ventilation and emergency medicine. Tracheal tubes can be used to ensure an adequate exchange of oxygen and carbon dioxide, to deliver oxygen in higher concentrations than found in air, or to administer gases to a subject.

An endotracheal tube is a specific type of tracheal tube that is usually inserted through the mouth or nose. It is a breathing conduit designed to be placed into the airway of critically injured, ill or anesthetized subjects in order to perform positive pressure ventilation of the lungs and to prevent the possibility of aspiration or airway obstruction.

Intubation generally refers to the placement of a tracheal tube into the trachea of a subject to maintain an open airway, provide ventilatory assistance, or to serve as a conduit through which to administer certain drugs. Intubation is generally performed in critically injured, ill or anesthetized subjects to facilitate ventilation of the lungs and to prevent the possibility of asphyxiation or airway obstruction.

Methods to confirm proper tracheal tube placement include direct visualization during insertion as the tip of the tracheal tube passes through the glottis or indirect visualization of the tracheal tube within the trachea using a device such as a bronchoscope. If a tracheal tube is properly placed, equal bilateral breath sounds may be heard when listening to the chest of a subject with a stethoscope. This technique may be referred to as an auscultation of the chest. Further, equal bilateral rise and fall of the chest wall will be apparent with ventilatory excursions when the tracheal tube is properly placed into the trachea. If breath sounds are heard when listening to the area over a subject's stomach, this may indicate an improper placement of the tracheal tube into the esophagus. When the tube is properly placed, a small amount of water vapor may be evident within the lumen of the tracheal tube with each exhalation and there should be no gastric contents in the tracheal tube at any time.

Capnography has emerged as an important tool for confirmation of proper tube placement within the trachea. Other methods to detect tracheal tube placement using instruments include the use of a colorimetric end-tidal carbon dioxide detector and transthoracic impedance detection.

SUMMARY

Various aspects of examples of the invention are set out in the claims. According to a first aspect of the present invention, a ventilation monitoring device comprises at least one processor and at least one memory including computer program code. The at least one memory and the computer program code are configured with at least one processor to cause the ventilation monitoring device to determine whether an intubated subject's tracheal tube is properly placed by receiving an indication of a subject's breath from at least one sensor.

According to a second aspect of the present invention, a method for determining whether a subject's tracheal tube is properly placed comprises receiving an indication of a subject's breath from at least one sensor and receiving an indication of a positive result of an auscultation by a ventilation monitoring device comprising at least one processor and at least one memory including computer program code.

According to a third aspect of the present invention, a system comprises a capnography sensor configured to detect a partial pressure of carbon dioxide in a subject's breathing gases, at least two electrodes and a medical monitoring device electrically coupled with the capnography sensor and the at least two electrodes. The medical monitoring device comprises at least one processor, at least one memory including computer program code. The memory and the computer program code is configured with the at least one processor, the capnography sensor and the electrodes to cause the medical monitoring device to determine whether an intubated subject's tracheal tube is properly placed by receiving an indication of a subject's breath from at least one of the capnography sensor or the at least two electrodes.

In another aspect, a ventilation monitoring device includes at least one processor, and at least one memory including computer program code. The at least one memory and the computer program code being configured with the at least one processor to cause the ventilation monitoring device to determine whether an intubated subject's tracheal tube is properly placed by receiving an indication of a subject's breath from at least one of a capnography sensor or at least two electrodes configured with the ventilation monitoring device to measure a transthoracic impedance of the subject, and receiving an indication of a positive result of an auscultation within a predetermined time limit.

Implementations may include one or more of the following features. The ventilation monitoring device may further include a graphical user interface. The indication of a positive result of an auscultation may be received via the graphical user interface. The indication of a positive result of an auscultation may include an indication of an auscultation of a subject's left lung, right lung, left axillary, right axillary or abdomen. The ventilation monitoring device may provide a prompt to a user upon expiration of the predetermined time limit. Indication of the subject's breath from the capnography sensor may be selectable from a graphical user interface. Indication of the subject's breath from the at least two electrodes may be selectable from a graphical user interface. Indication of the subject's breath from the capnography sensor and from the at least two electrodes may be selectable from a graphical user interface. The device may further include an electrocardiogram (ECG) monitoring unit. The device may further include a defibrillation unit.

In another aspect, a method for determining whether a subject's tracheal tube is properly placed includes receiving within a ventilation monitoring device an indication of a subject's breath from at least one of a capnography sensor or at least two electrodes configured with the ventilation monitoring device to measure a transthoracic impedance of the subject. The method also includes receiving within the ventilation monitoring device an indication of a positive result of an auscultation. Receiving the indication of the positive result of the auscultation occurs within a predetermined time limit.

Implementations may include one or more of the following features. A graphical user interface may be configured to receive the at least one indication of a positive result of an auscultation. The indication of the positive result may be related to an auscultation of a left lung, right lung, left axillary, right axillary or abdomen. The method may include prompting a user upon expiration of the predetermined time limit. Indication of the subject's breath from the capnography sensor may be selectable from a graphical user interface. Indication of the subject's breath from the at least two electrodes may be selectable from a graphical user interface. Indication of the subject's breath from the capnography sensor and from the at least two electrodes may be selectable from a graphical user interface.

In still another aspect, one or more computer readable media storing instructions that are executable by a processing device, and upon such execution cause the processing device to perform operations that include receiving within a ventilation monitoring device an indication of a subject's breath from at least one of a capnography sensor or at least two electrodes configured with the ventilation monitoring device to measure a transthoracic impedance of the subject. Operations also include receiving within the ventilation monitoring device an indication of a positive result of an auscultation. Receiving the indication of the positive result of the auscultation occurs within a predetermined time limit.

Implementations may include one or more of the following features. A graphical user interface may be configured to receive the at least one indication of a positive result of an auscultation. The indication of the positive result may be related to an auscultation of a left lung, right lung, left axillary, right axillary or abdomen. The computer readable media may further store instructions that are executable by the processing device, and upon such execution cause the processing device to perform operations that may include prompting a user upon expiration of the predetermined time limit. Indication of the subject's breath from the capnography sensor may be selectable from a graphical user interface. Indication of the subject's breath from the at least two electrodes may be selectable from a graphical user interface. Indication of the subject's breath from the capnography sensor and from the at least two electrodes may be selectable from a graphical user interface. The computer readable media may further store instructions that are executable by the processing device, and upon such execution cause the processing device to perform operations that may include electrocardiogram (ECG) monitoring of the subject. The computer readable media may further store instructions that are executable by the processing device, and upon such execution cause the processing device to perform operations that may include initiating defibrillation the subject.

BRIEF DESCRIPTION OF THE DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings.

DETAILED DESCRIPTION

Figure 1:
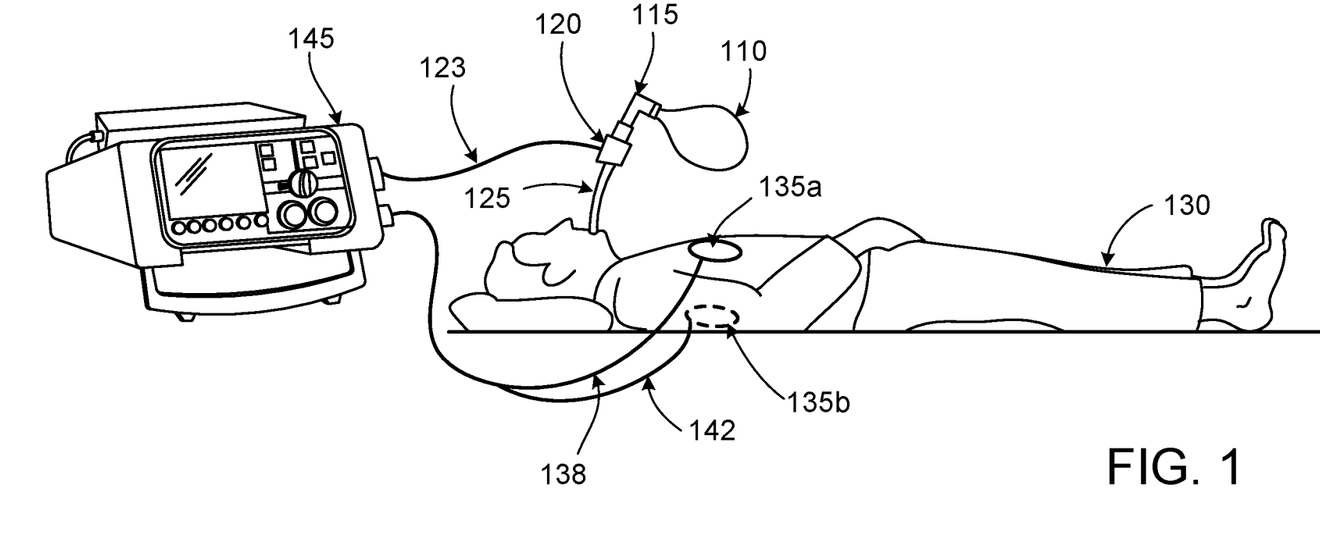
FIG. 1 is a diagram showing a ventilation monitoring device and a subject intubated with an endotracheal tube according to an example embodiment of the invention.

FIG. 1 is a diagram showing ventilation monitoring device 145 and subject 130 intubated with an endotracheal tube 125 according to an example embodiment of the invention. A tracheal tube is a catheter that is inserted into the trachea of subject 130 to establish and maintain an open airway and to ensure adequate exchange of oxygen and carbon dioxide. An endotracheal tube such as endotracheal tube 125 is a specific type of tracheal tube that is usually inserted through the subject's mouth or nose. Many types of tracheal tubes such as endotracheal tube 125 may be used with embodiments of the present invention. For example, airway management tubes from King Systems of Noblesville, Ind. such as the King LT(S)-D airway tube or the Combitube™ from Covidien of Mansfield, Mass. may be used.

Ventilation bag 110 coupled with the ventilation bag connector 115, capnography sensor 120 and endotracheal tube 125 allows air to be forced into the subject's lungs as ventilation bag 110 is squeezed. Ventilation bag 110 may be equipped with a valve to allow the subject's exhalation gases to be released into the air without the possibility of backflow into ventilation bag 110. The assembly permits gases exchanged with the subject's lungs to flow through and be monitored by capnography sensor 120.

A capnography sensor such as capnography sensor 120 monitors the concentration or partial pressure of carbon dioxide ($CO_2$) in the respiratory gases of the subject. Capnography sensor 120 communicates information related to the subject's respiratory gases such as $CO_2$ concentration in mm HG, end-tidal $CO_2$, inspired $CO_2$ and respiratory rate to ventilation monitoring device 145 through communication cable 123. Many capnography sensors on the market today may be used with embodiments of the present invention including but not limited to the Capnostat® 3 or Capnostat® 5 Mainstream $CO_2$ Sensors manufactured by Respironics, Inc. of Murrysville, Pa.

Communication cable 123 may be any type of communication cable or set of wires, which allows data to be exchanged between ventilation monitoring device 145 and capnography sensor 123 such as but not limited to an RS-232 cable, Universal Serial Bus (USB) cable or Ethernet cable. Communication between ventilation monitoring device 145 and capnography sensor 123 may be a wireless communication channel such as but not limited to IEEE 802.11 wireless local area network (WLAN) or low-power radio frequency (RF) communication such as Bluetooth.

Embodiments of the present invention utilize principles as described in U.S. Pat. No. 7,925,339, which is incorporated herein in its entirety by reference. Electrodes 135a and 135b are electrically coupled with ventilation monitoring device 145 using cables 138 and 142, respectively, as shown in FIG. 1. Electrodes 135a and 135b are positioned across the subject's thoracic cavity and attached to the subject, one electrode anterior and the other electrode posterior, for example. In the embodiment, electrodes 135a and 135b are electrocardiogram (ECG) signal pickup electrodes, but electrodes 135a and 135b may be any type of suitable electrodes capable of measuring a thoracic impedance of a subject. The ventilation monitoring device 145 is configured with electrodes 135a and 135b to monitor changes in the transthoracic impedance of subject 130. If endotracheal tube 125 is properly placed in the subject's trachea and the subject's lungs are ventilated using ventilation bag 110, ventilation monitoring device 145 will detect a change in impedance across the subject's thorax between electrodes 135a and 135b. If the endotracheal tube 125 has not been properly placed, for example, it was placed in the subject's esophagus, or has become dislodged, ventilation monitoring device 145 will not measure any significant impedance change across the subject's thorax and a corresponding indication may be conveyed to the user.

Figure 2:
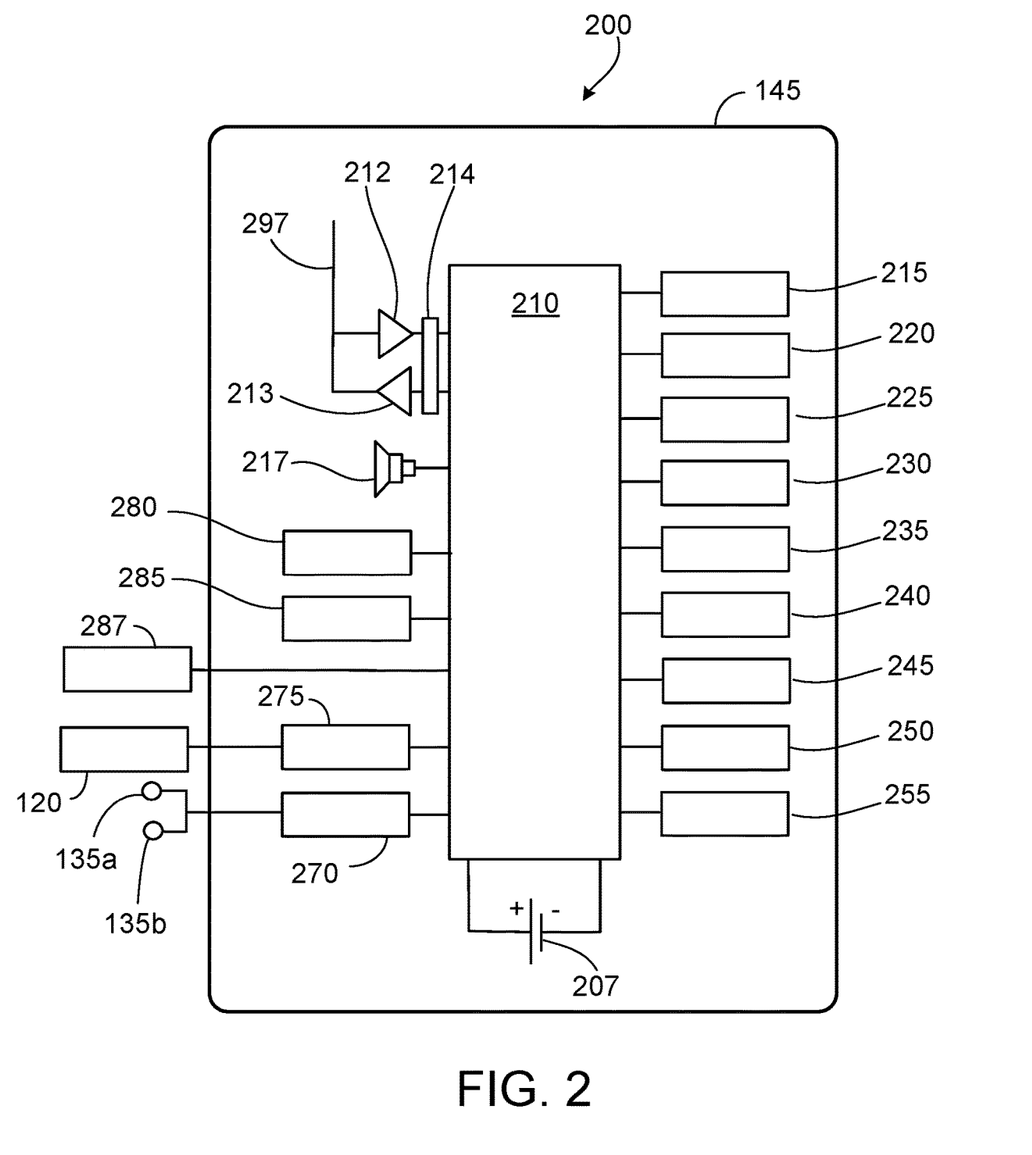
FIG. 2 is a block diagram of a system comprising a ventilation monitoring device, capnography sensor and electrodes according to an example embodiment of the invention.

FIG. 2 is a block diagram of system 200 comprising ventilation monitoring device 145, capnography sensor 120 and electrodes 135a and 135b according to an example embodiment of the invention. In an embodiment, ventilation monitoring device 145 is a dedicated ventilation monitor comprising embodiments of the present invention for at least the purpose of determining whether a subject's tracheal tube is properly placed. In another embodiment, ventilation monitoring device 145 is a part of a medical monitor and/or defibrillator such as the Zoll E-Series Monitor Defibrillator manufactured by Zoll Medical Corporation of Chelmsford, Mass., which further comprises embodiments of the present invention.

In the embodiment, ventilation monitoring device 145 comprises at least one processor such as processor 210 and at least one memory such as volatile memory 225 or a non-volatile memory 230 including computer program code, which is configured to determine whether a subject's tracheal tube is properly placed. Volatile memory 225 and/or a non-volatile memory 230 may be removable by a user.

Volatile memory 225 may comprise a cache area for the temporary storage of data. Non-volatile memory 230 may further comprise an electrically erasable programmable read only memory (EEPROM), flash memory, and/or the like. In an embodiment, ventilation monitoring device 145 may use memory to store information and/or data including computer program code to implement one or more features of ventilation monitoring device 145 including but not limited to computer program code for determining whether an intubated subject's tracheal tube is properly placed.

Ventilation monitoring device 145 may comprise at least one processor such as processor 210 and at least one other processing component. Processor 210 may comprise circuitry for implementing medical monitoring features such as determining whether an intubated subject's tracheal tube is properly placed as well as other medical monitor functionality. For example, the at least one processor 210 may comprise a digital signal processor device, a microprocessor device, a digital to analog converter, other support circuits, and/or the like. Further, the processor 210 may comprise features to operate one or more software programs. In an embodiment, the processor 210 may be capable of operating at least one software program to implement functionality for determining whether an intubated subject's tracheal tube is properly placed. For example, the at least one software program may comprise a connectivity program to allow the ventilation monitoring device 145 to transmit and receive Internet and/or cellular data over a wired or wireless medium, such as but not limited to voice, text, email messages, location-based content, web page content, fax content and/or the like.

In an embodiment, the ventilation monitoring device 145 comprises at least one antenna 297 to communicate with a transmitter 213 and a receiver 212. Transmitter 213 and/or receiver 212 are coupled with a network interface 214 for transmitting and receiving data with devices such as other medical equipment or emergency medical services centers. Processor 210 may be configured to provide at least one signal to the transmitter 213 and receive at least one signal from receiver 212. Further, transmitter 213 and/or receiver 212 coupled with network interface 214 may be configured to transmit and receive analog and/or digital voice communications such as with emergency medical personnel.

The ventilation monitoring device 145 may further comprise an identifier, such as international mobile equipment identification (IMEI) code, capable of uniquely identifying itself. For example, the processor 210, using the stored instructions, may determine an identity, e.g., using cell identification information.

Figure 3:
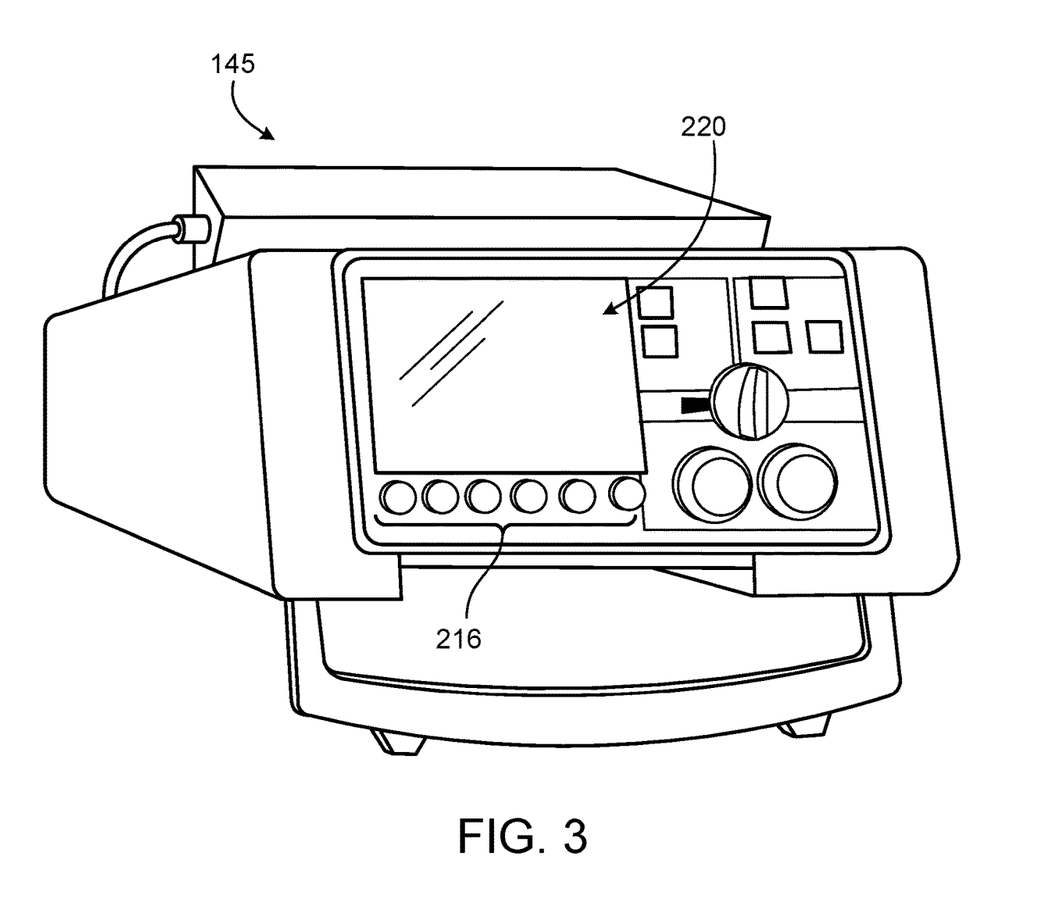
FIG. 3 is a diagram of a ventilation monitoring device according to an example embodiment of the invention.

Ventilation monitoring device 145 further comprises a user interface 215, which may include at least one input and/or output device coupled with processor 210 such as but not limited to a display such as display 220, touch screen, keyboard, keypad, mouse and/or the like. In an embodiment, display 220 shown in FIG. 2 and FIG. 3 coupled with processor 210 is capable of displaying at least one of an indication of a subject's breath, a representation of a subject's breathing pattern and information related to a determination of whether an intubated subject's tracheal tube is properly placed. In an embodiment, a keypad, keyboard, buttons and/or other input features such as soft keys 216 of FIG. 3 enables a user to configure ventilation monitoring device 145 to perform functions such as confirming whether a breath has been detected during an auscultation. Further, the keypad or keyboard may enable a user to compose text-based messages and communicate with other users such as emergency medical personnel.

In an embodiment, ventilation monitoring device 145 further comprises a speaker 217 and/or a microphone 280. Speaker 217, for example, may enable the ventilation monitoring device to provide voice instructions to a user. Microphone 280, for example, may enable a user to speak with emergency medical personnel via network interface 214 at an emergency response facility.

In an embodiment, ventilation monitoring device 145 is a medical monitoring device further comprising features such as electrocardiogram (ECG) monitoring and/or defibrillation. For example, ventilation monitoring device 145 may comprise ECG monitoring unit 235 and/or defibrillation unit 240. In an embodiment, ventilation monitoring device 145 further comprises at least one power supply such as battery 207 for providing power to ventilation monitoring device 145 and/or for charging defibrillation unit 240. Ventilation monitoring device 145 may further comprise a location determining unit 245. Location determining unit 245 may comprise a global positioning system (GPS) receiver 250 for receiving a geographic location of ventilation monitoring device 145. Location determining unit 245 may use cell identification information, for example, to determine a geographic location for ventilation monitoring device 145. Ventilation monitoring device 145 may further comprise programmable timer 255 for determining intervals of time such as a time period between indications of a subject's breath.

System 200 may comprise a capnography sensor 120 and/or electrodes 135a and 135b. In some embodiments, either a capnography sensor or electrodes configured with system 200 to determine transthoracic impedance may be used to detect a subject's breath. In some embodiments, both a capnography sensor and electrodes may be used simultaneously with system 200 to detect a subject's breath. Using both a capnography sensor and electrodes together may increase the reliability of breath detection. For example, if a capnography sensor such as capnography sensor 120 becomes dislodged from the subject tracheal or malfunctions, electrodes 135a and 135b may be used as a fallback or redundant means to detect a subject's breath. Likewise, if either electrodes 135a or 135b become disconnected from the subject, capnography sensor 120 may be used as a fallback or redundant means to detect a subject's breathe.

When capnography sensor 120 is used with system 200, processor 210 may configure and/or calibrate capnography sensor 120 for use with ventilation monitoring device 145. In an embodiment, processor 210 is configured with at least one memory such as non-volatile memory 225 to detect at least one indication of a subject's breath by receiving information related to the subject's respiratory gases such as $CO_2$ concentration, end-tidal $CO_2$, inspired $CO_2$ and respiratory rate from capnography sensor 120. In the embodiment, ventilation monitoring device 145 may comprise a capnography sensor interface 275, which may include a device driver configured with processor 210 to read one or more memory locations from capnography sensor 120 in order to receive at least one indication of the subject's breath.

When electrodes 135a and 135b are used with system 200 to measure transthoracic impedance, processor 210 may initially configure and/or calibrate electrodes 135a and 135b for use with ventilation monitoring device 145. In an embodiment, processor 210 is configured with at least one memory to detect at least one indication of a subject's breath by receiving impedance information from electrode 135a and 135b via electrodes interface 270 using principles described in U.S. Pat. No. 7,925,339, which has been incorporated herein by reference.

In some embodiments, an indication from capnography sensor 120 of a subject's breath alone is sufficient evidence for processor 200 to determine that an intubated subject's tracheal tube is properly placed. In some embodiments, an indication via electrodes 135a and 135b of a subject's breath alone is sufficient evidence for processor 200 to determine that an intubated subject's tracheal tube is properly placed. In some embodiments, an indication of a subject's breath from both capnography sensor 120 and via electrodes 135a and 135b is required for processor 200 to determine that an intubated subject's tracheal tube is properly placed. In some embodiments, an indication from at least one of capnography sensor 120 and electrodes 135a and 135b along with a confirmation from a user of a positive result of at least one auscultation is required for processor 200 to determine that an intubation subject's tracheal tube is properly placed.

In some embodiments, the term "auscultation" as used herein means manual auscultation performed by a medical professional in the conventional sense. In some embodiments, acoustic cardiography performed by a device such as an Audicor® manufactured by Inovise Medical, Inc. of Portland, Oreg. may be used in place of manual auscultation to determine breath sounds or in some cases, a lack thereof. As such, "auscultation" as used herein may mean utilizing a device such as an Audicor® to perform a diagnostic technique such as cardiography on a subject to record and algorithmically interpret acoustical data to determine evidence of breath sounds or a lack thereof.

In an embodiment, ventilation monitoring device 145 comprises at least one accelerometer such as accelerometer 285 coupled with processor 210 for detecting movement of the ventilation monitoring device 145. In an embodiment, system 200 comprises an accelerometer such as accelerometer 287, which is external to but communicatively coupled with ventilation monitoring device 145 capable of detecting movement of subject 130. For example, accelerometer 287 may be coupled with capnography sensor 120, tracheal tube 125, subject 130, the subject's stretcher or bed or other locations on or near subject 130. In an embodiment, the at least one processor 210 and at least one memory 225 including computer program code are configured to receive a value from accelerometer 285 and/or accelerometer 287 related to motion of ventilation monitoring device 145 and/or subject 130, respectively, and provide a prompt to a user when the value exceeds a predetermined threshold. For example, a value from an accelerometer which exceeds a predetermined threshold may indicate that subject 130 and/or ventilation monitoring device 145 received one or more mechanical shocks, for example, if ventilation monitoring device 145 or a stretcher carrying subject 130 was bumped against a wall during emergency transportation of subject 130. In the embodiment, a user may be prompted to inspect the subject's tracheal tube or execute ventilation monitor testing using ventilation monitoring device 145 to be sure the tracheal tube did not become dislodged.

Figure 4:
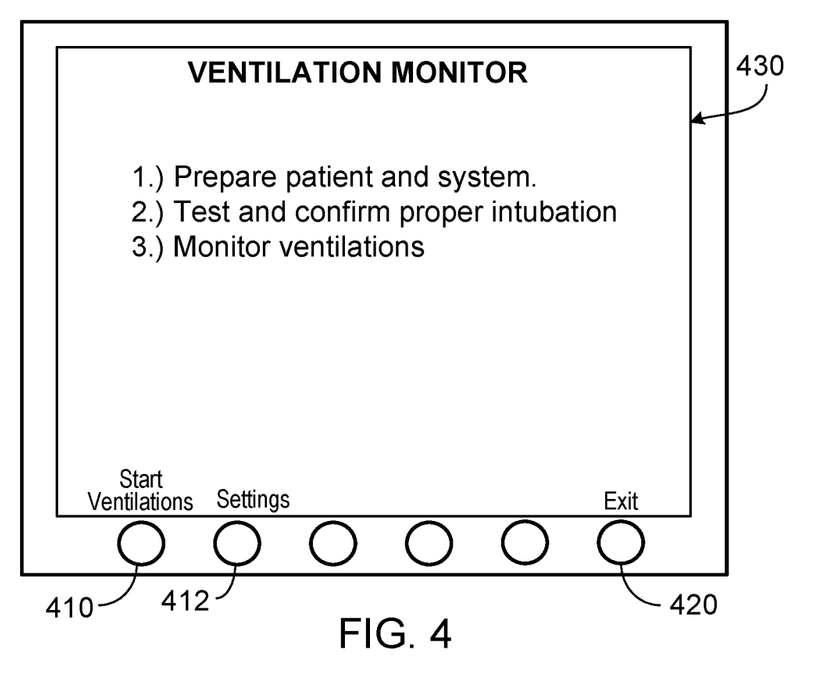
FIG. 4 is a diagram of an initial screen of a ventilation monitoring device according to an example embodiment of the invention.

FIG. 4 shows an initial screen 430 of the ventilation monitoring device 145 of FIG. 1 according to an example embodiment of the invention. If ventilation monitoring device 145 is a dedicated ventilation monitor comprising embodiments of the present invention, an initial screen such as initial screen 430 may be displayed after ventilation monitoring device 145 is powered-up and completes a self-test. Alternatively, if ventilation monitoring device 145 is a part of a medical monitor and/or defibrillator which further comprises embodiments of the present invention, an initial screen such as initial screen 430 may be displayed at any point when the user selects the ventilation monitor feature on the device.

An initial screen of ventilation monitoring device 145 may comprise, for example, instructions to be performed by a user, user interface configurable parameters, status and/or the like. In an embodiment, initial screen 430 comprises instructions informing a user of ventilation monitoring device 145 to (1) prepare the subject and ventilation monitoring system, (2) test and confirm that the subject was intubated properly and (3) monitor ventilations.

In an embodiment, initial screen 430 further comprises a set of menu options "start ventilations", "Settings" and "Exit", which correspond to buttons 410, 412 and 420, respectively. Buttons 410, 412 and 420 may be known as "soft keys" in the art since each key may correspond to multiple functions such that the present function of each key is related to the screen the user is presently viewing. The present function of a soft key such as soft key 412 is indicated by the description such as "Settings", which is located adjacent to the button.

In the embodiment, the user presses "Start Ventilations" soft key 410 once the subject has been intubated and ventilation monitoring is to begin. A user may press the "Exit" soft key 420 to end ventilation monitoring.

Figure 5:
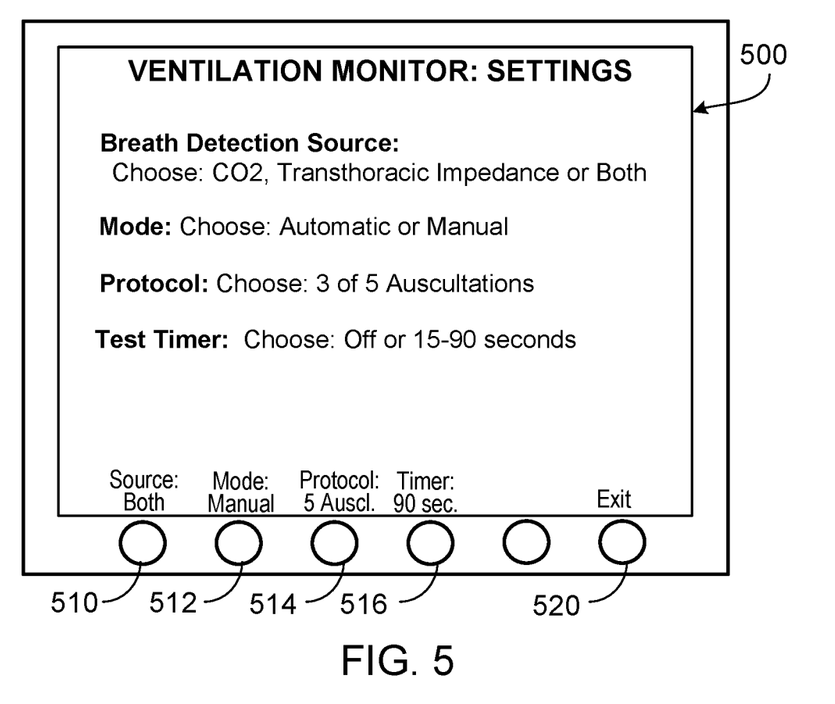
FIG. 5 is a diagram of a settings screen of a ventilation monitoring device according to an example embodiment of the invention.

FIG. 5 is a diagram of a settings screen 500 of a ventilation monitoring device 145 according to an example embodiment of the invention. In a settings screen such as settings screen 500, a user may modify one or more parameters related to the configuration of ventilation monitoring device 145. In the embodiment, soft key 510 corresponding to the configurable parameter, "Source" enables a user to specify whether a capnography sensor, electrodes or both a capnography sensor and electrodes will be used with ventilation monitor. Further, "Source" may enable a user to specify that "either" the capnography sensor or electrodes may determine that a breath has been detected.

In the embodiment, soft key 512 corresponding to the configurable parameter, "Mode", may be used to set the ventilation monitor device 145 to a manual mode or automatic mode. In a manual mode, a user must press a "confirm" soft key for each auscultation performed on the subject, which indicates a positive result. In an automatic mode, a user may press a "confirm" soft key only once when all auscultations are performed on the subject and corresponding breaths were detected during each auscultation.

In the embodiment, soft key 514 enables a user to set the number of auscultations, which will be performed to 3 or 5. If a user chooses 3 auscultations, then ventilation monitor device 145 will prompt the user to auscultate the subject's left lung, right lung and abdomen. If a user chooses 5 auscultations, then ventilation monitor device 145 will prompt the user to auscultate the subject's left lung, left axillary right lung, right axillary and abdomen.

In the embodiment, soft key 516 configures a timer for all tests performed. In the embodiment, timer such as timer 255 of FIG. 2 may be set to 15, 30, 45, 60 or 90 seconds. In the embodiment, all of the tests being performed on the subject must be completed within the configured time limit or else a failure status for the testing will be reported. In another embodiment, each one of the tests being performed on the subject must be completed within the configured time limit or else a failure status for the testing will be reported. In this embodiment, the timer may be reset after each successful test. A user may press the "Exit" soft key 520 to exit the settings screen.

Figure 6:
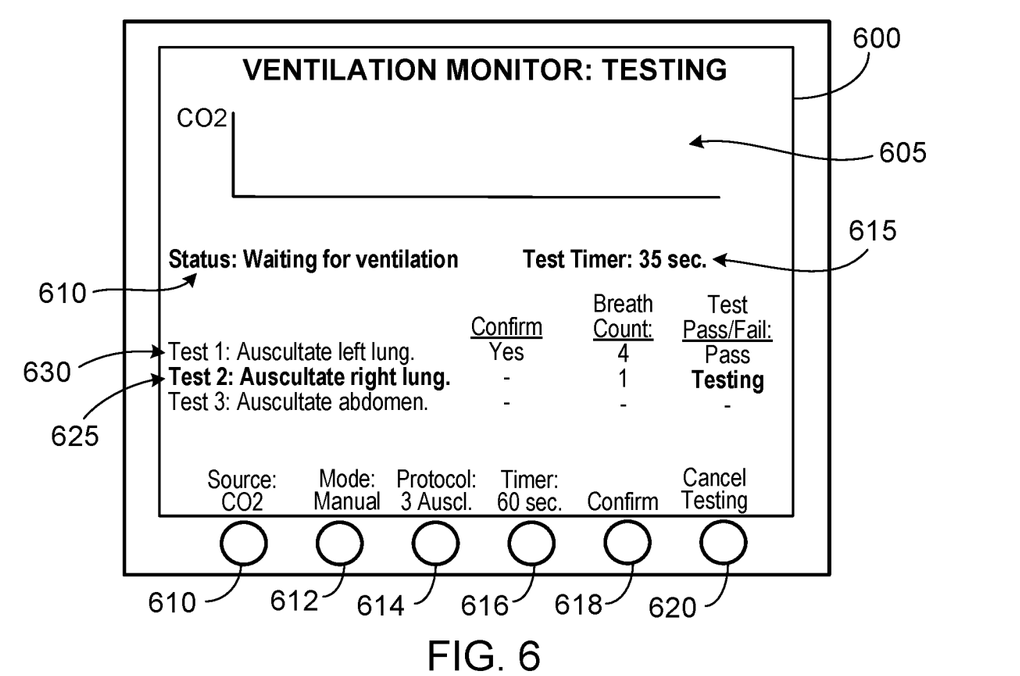
FIG. 6 is a diagram of a testing screen of a ventilation monitoring device showing testing in progress, the ventilation monitoring device configured in a manual mode for use with a capnography sensor and protocol comprising three auscultations according to an example embodiment of the invention.

FIG. 6 is a diagram of a testing screen 600 of ventilation monitoring device 145 showing testing in progress, ventilation monitoring device 145 configured in a manual mode for use with capnography sensor 120 and a protocol comprising three auscultations according to an example embodiment of the invention. In the embodiment, the source is configured to "$CO_2$" using soft key 610, which means that only the capnography sensor 120 of FIGS. 1 and 2 will be used as an automated means to detect the subject's breath. Manual mode, which requires the user to confirm a positive result of each auscultation performed using soft key 618, is configured by the user using soft key 612. The 3-auscultation protocol, which includes user auscultations of the left lung, right lung and abdomen, is configured by the user using soft key 614. At any point, the testing may be canceled by using soft key 620.

In the embodiment, since the capnography sensor 120 is being used with ventilation monitoring device 145, capnograph 605 is displayed on testing screen 600. If a capnography sensor was not being used, i.e., "Source" corresponding to soft key 610 was configured to "Electrodes", then a capnograph would not be displayed and a transthoracic impedance graph would be displayed instead. If both the capnography sensor 120 and electrodes 135a and 135b were being used i.e. "Source:" was configured to "both", then both the capnograph and transthoracic impedance graph may be displayed on screen 600.

According to testing screen 600, the present status 610 of the testing indicates "Waiting for ventilation", which means that ventilation monitoring device 145 is waiting for capnography sensor 120 to detect a positive air flow from ventilation bag 110 of FIG. 1. The results of Test 1 630 indicate that the test passed. The results of Test 1 630 further show that a confirmation was provided by the user that subject's left lung was auscultated and 4 breaths were detected by capnography sensor 120.

Further, according to testing screen 600, the result of Test 2 625 indicates that capnography sensor 120 detected 1 breath, however, since the user has not confirmed a breath from auscultation of the right lung, test 2 has not completed. Test timer 255, which was originally set to 60 seconds using soft key 616, indicates that there are 35 seconds left in the overall testing period including the time to complete Test 2 and Test 3. If Test 2 and Test 3 are not completed within the time period left, which is 35 seconds, then the overall testing will fail and Status 610 will report "Failed" and the reasons for the failure.

Figure 7:
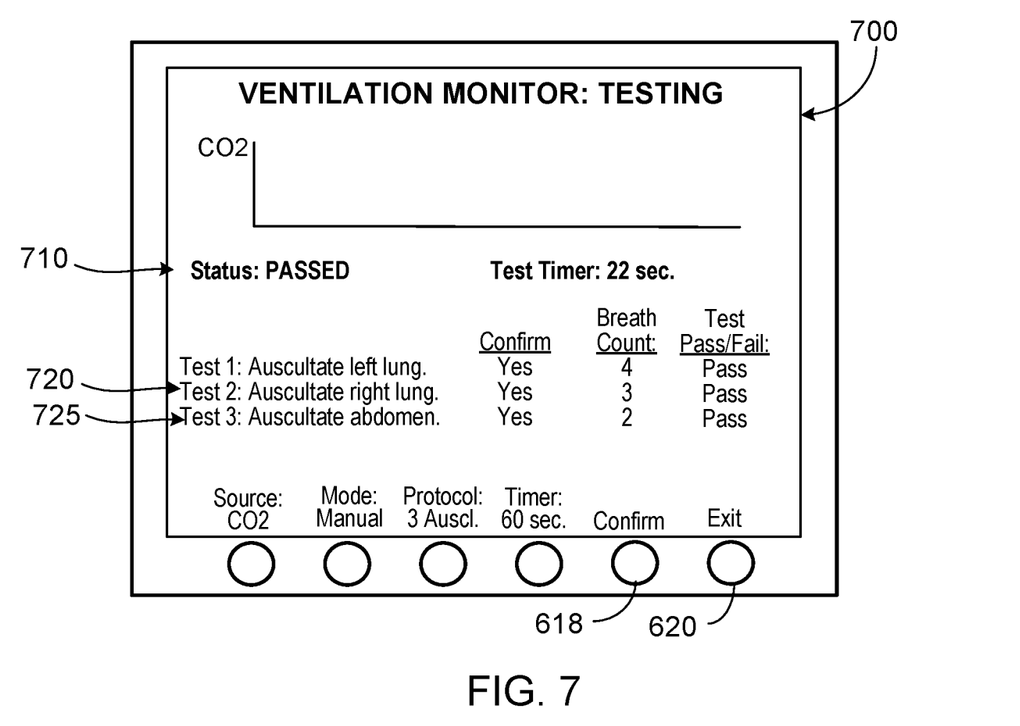
FIG. 7 is a diagram of a testing screen on a ventilation monitoring device showing the testing has passed, the ventilation monitoring device configured in a manual mode for use with a capnography sensor and a protocol comprising three auscultations according to an example embodiment of the invention.

FIG. 7 is a diagram of a testing screen 700 on ventilation monitoring device 145 showing the testing has passed, the ventilation monitoring device 145 configured in a manual mode for use with capnography sensor 120 and a protocol comprising three auscultations according to an example embodiment of the invention. In the embodiment, screen 700 shows a continuation of the testing as shown in screen 600 of FIG. 6. According to screen 700, the results of Test 2 720 indicate that the user has confirmed with soft key 618 that the subject's right lung has been auscultated and at least one breath was detected. Further, since capnography sensor 120 has detected at least one breath, 3 breaths in this case, Test 2 has passed.

In the embodiment, the results of Test 3 725 indicate that the user has confirmed with soft key 618 that the subject's abdomen has been auscultated and no breathing was detected. Further, since capnography sensor 120 has detected at least one breath, 2 breaths in this case, Test 3 has passed. Since each of Test 1, Test 2 and Test 3 have passed; overall status 710 indicates that the testing has passed. In an embodiment, the results of the overall testing including the results of each of the Tests, e.g. Test 1, Test 2 and Test 3, are saved in memory, for example, in a FLASH memory such as non-volatile memory 230 of FIG. 2. At this point, the user may exit the Ventilation Monitor Testing by pressing soft key 620.

Figure 8:
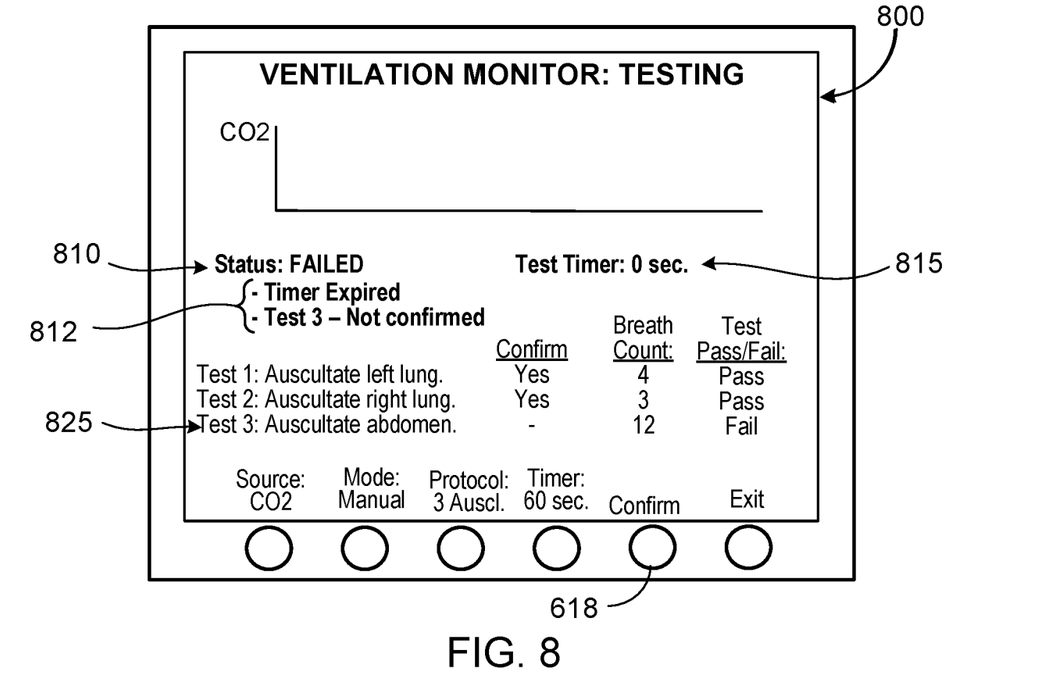
FIG. 8 is a diagram of a testing screen on a ventilation monitoring device showing that the testing has failed, the ventilation monitoring device configured in a manual mode for use with a capnography sensor and a protocol comprising three auscultations according to an example embodiment of the invention.

FIG. 8 is a diagram of a testing screen 800 on ventilation monitoring device 145 showing that the testing has failed, the ventilation monitoring device 145 configured in a manual mode for use with capnography sensor 120 and a protocol comprising three auscultations according to an example embodiment of the invention. In the embodiment, screen 800 shows a continuation of the testing as shown in screen 600 of FIG. 6.

In the embodiment, the results of Test 3 825 indicate that the test has failed, which has caused the overall testing Status 810 to indicate failure. Although the capnography sensor 145 detected 12 breaths of the subject, the user did not confirm a positive result of the subject's abdominal auscultation in Test 3 using soft key 618 within the timer period. As a result, test timer 255 counted down to 0 as indicated at 815 and the overall testing failed. Reasons for the failure of the overall testing 812 indicate that the timer expired and that a confirmation in Test 3 was not received.

Figure 9:
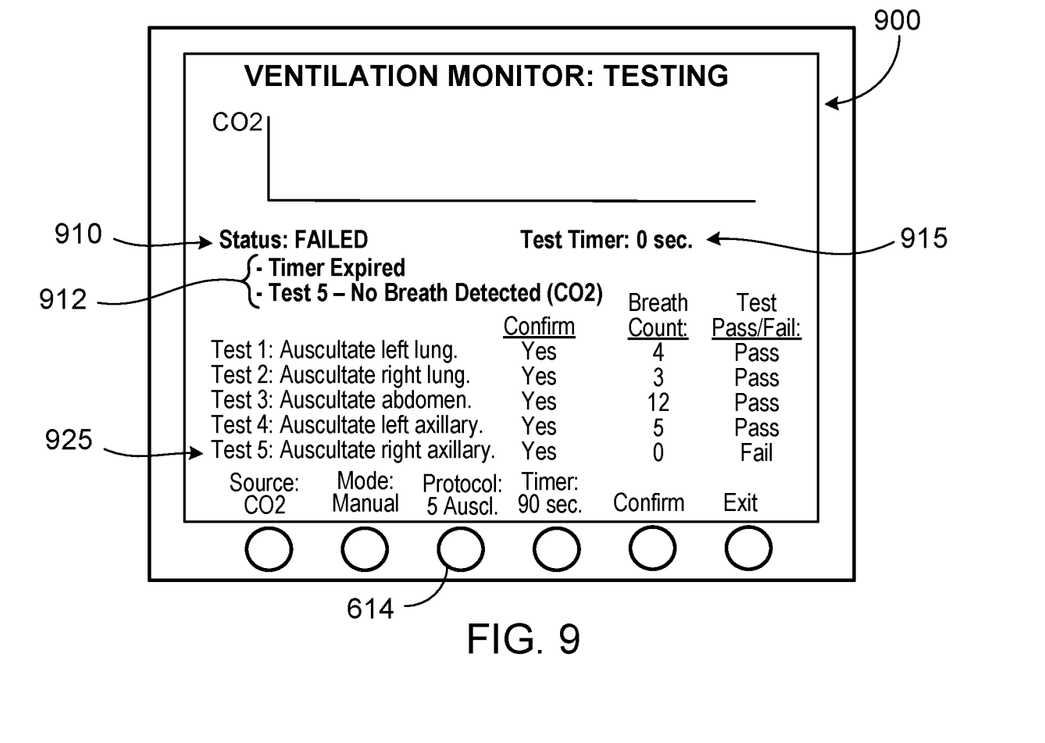
FIG. 9 is a diagram of a testing screen on a ventilation monitoring device showing that the testing has failed, the ventilation monitoring device configured in a manual mode for use with capnography sensor and a protocol comprising five auscultations according to an example embodiment of the invention.

FIG. 9 is a diagram of a testing screen 900 on ventilation monitoring device 145 showing that the testing has failed, the ventilation monitoring device 145 configured in a manual mode for use with capnography sensor 120 and a protocol comprising five auscultations according to an example embodiment of the invention. In the embodiment, screen 900 shows that a user configured the ventilation monitor testing using soft key 614 to require 5 auscultations to be performed on the subject including auscultations of the subject's left lung, right lung, abdomen, left axillary and right axillary.

Testing screen 900 shows that Tests 1 through 4 have passed, however, Test 5 has failed. In Test 5 925, although the user confirmed that at least one breath was detected during auscultation of the subject's right axillary, capnography sensor 120 did not detect at least one breath. Screen 900 shows the results of Test 5 925, which indicate that the subject's breath count did not increment (remained at 0) and Test 5 failed as a result. The failure of a capnography sensor to detect a breath may be due to a number of reasons such as endotracheal tube 125 of FIG. 1 becoming dislodged from the subject's trachea or the subject may have stopped breathing. As ventilation monitoring device 145 was waiting for capnography sensor 120 to detect a breath from subject 130, test timer 255 counted down to 0 as indicated at 915 and triggered a failure of the overall testing 910. Screen 900 further indicates that reasons 912 for the failure of the overall testing was that the timer expired and no breath was detected in Test 5.

Figure 10:
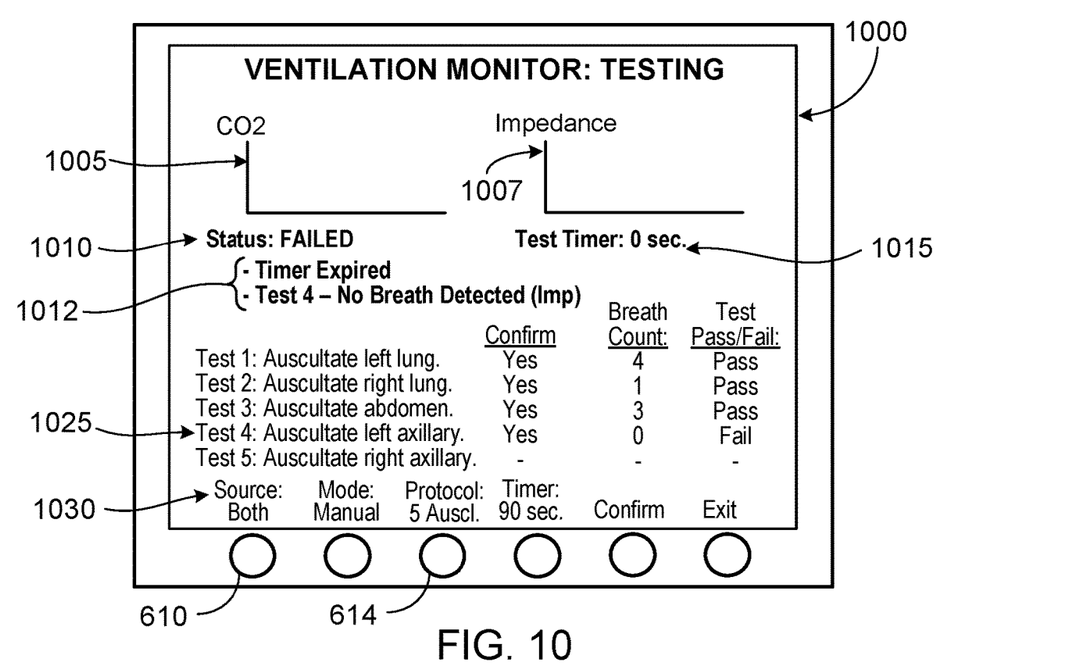
FIG. 10 is a diagram of a testing screen on a ventilation monitoring device showing that the testing has failed, the ventilation monitoring device configured in a manual mode for use with capnography sensor, electrodes, and a protocol comprising five auscultations according to an example embodiment of the invention.

FIG. 10 is a diagram of a testing screen 1000 on ventilation monitoring device 145 showing that the testing has failed, the ventilation monitoring device 145 configured in a manual mode for use with capnography sensor 120, electrodes 135a and 135b, and a protocol comprising five auscultations according to an example embodiment of the invention. In the embodiment, screen 1000 shows that a user configured the ventilation monitor testing using soft key 614 to require 5 auscultations to be performed on the subject including auscultations of the subject's left lung, right lung, abdomen, left axillary and right axillary. Further, screen 1000 shows that the user configured the source 610 to be both the capnography sensor 120 and electrodes 135a and 135b of FIG. 1. As a result, both a capnograph 1005 and transthoracic impedance waveform 1007 are shown in screen 1000.

Testing screen 1000 shows that Tests 1 through 3 have passed, however, Test 4 has failed. In Test 4, although the user confirmed that at least one breath was detected during auscultation of the subject's left axillary, system 200 configured with capnography sensor 120 and electrodes 135a and 135b indicted a failure to detect a breath from subject 130. Since source 1030 is set to "both", the system 200 must detect a breath from both capnography sensor 120 and electrodes 135a and 135b. Screen 1000 shows the results of Test 4 1025, which indicate that the subject's breath count did not increment (remained at 0) and Test 4 failed as a result. Screen 1000 further indicates that reasons 1012 for the failure of the overall testing was that the timer expired and no breath was detected in Test 4 with respect to the transthoracic impedance testing using electrode 135a and 135b. Since source 1030 was set to "both", even though system 200 may have detected a breath using capnography sensor 120, the overall testing failed since no breath was detected with respect to the transthoracic impedance testing.

The failure of the transthoracic impedance to detect a breath may be due to a number of reasons such as electrode 135a or electrode 135b becoming disconnected from the subject's chest or back or the subject may be in repertory distress. As ventilation monitoring device 145 was waiting for the transthoracic impedance testing using electrodes 135a and 135b to detect a breath from subject 130, test timer 1015 counted down to 0 and triggered a failure of the overall testing indicated at 1010.

In another embodiment, if source 1030 was set to "either" for example, a test such as Test 4 could pass providing that system 200 detected a breath using either capnography sensor 120 or transthoracic impedance testing and the user confirmed the presence of a breath by auscultation.

Figure 11:
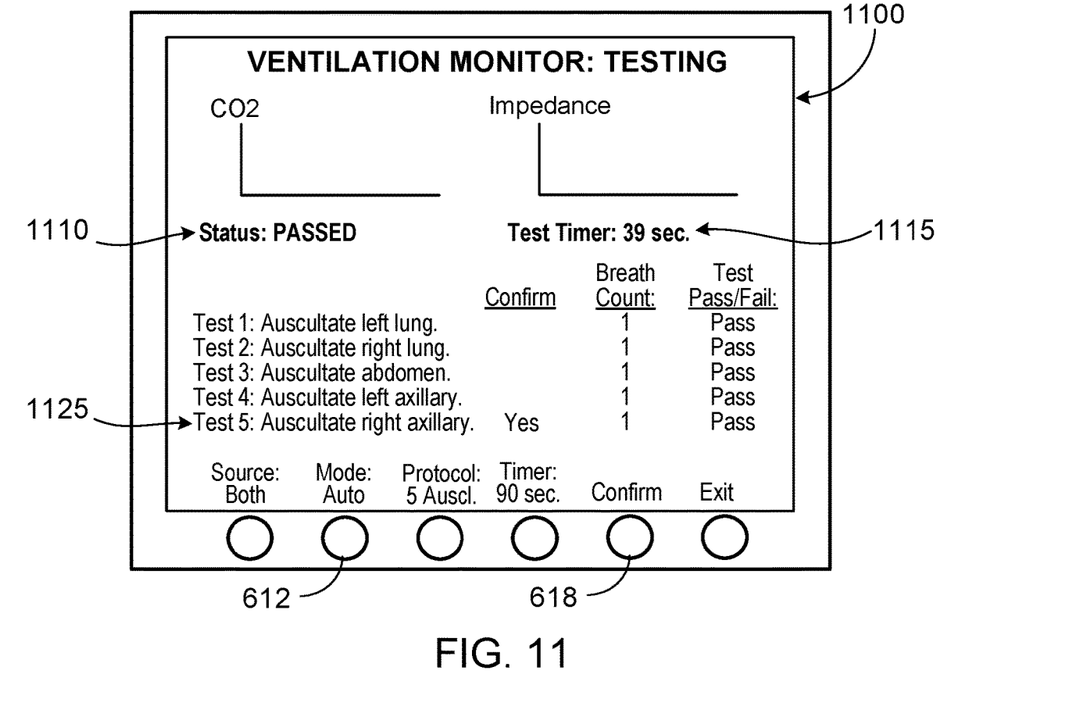
FIG. 11 is a diagram of a testing screen on ventilation monitoring device showing that the testing has passed, the ventilation monitoring device configured in an automatic mode for use with capnography sensor, electrodes, and a protocol comprising five auscultations according to an example embodiment of the invention.

FIG. 11 is a diagram of a testing screen 1100 on ventilation monitoring device 145 showing that the testing has passed, the ventilation monitoring device 145 configured in an automatic mode for use with capnography sensor 120, electrodes 135a and 135b, and a protocol comprising five auscultations according to an example embodiment of the invention.

Screen 1100 shows that the user configured the mode to be automatic using soft key 612. As a result, the user may confirm a positive result for each of the auscultations performed by pressing confirm soft key 618 once when the auscultations are completed but before the expiration of test timer 255 at indicated at 1115. For example, according to screen 1100 the user confirmed a positive result for each of the auscultations as indicated in result of Test 5 1125. Testing screen 1100 shows that each of Tests 1 through 5 has passed and the status 1110 for the testing indicates "Passed".

Figure 12:
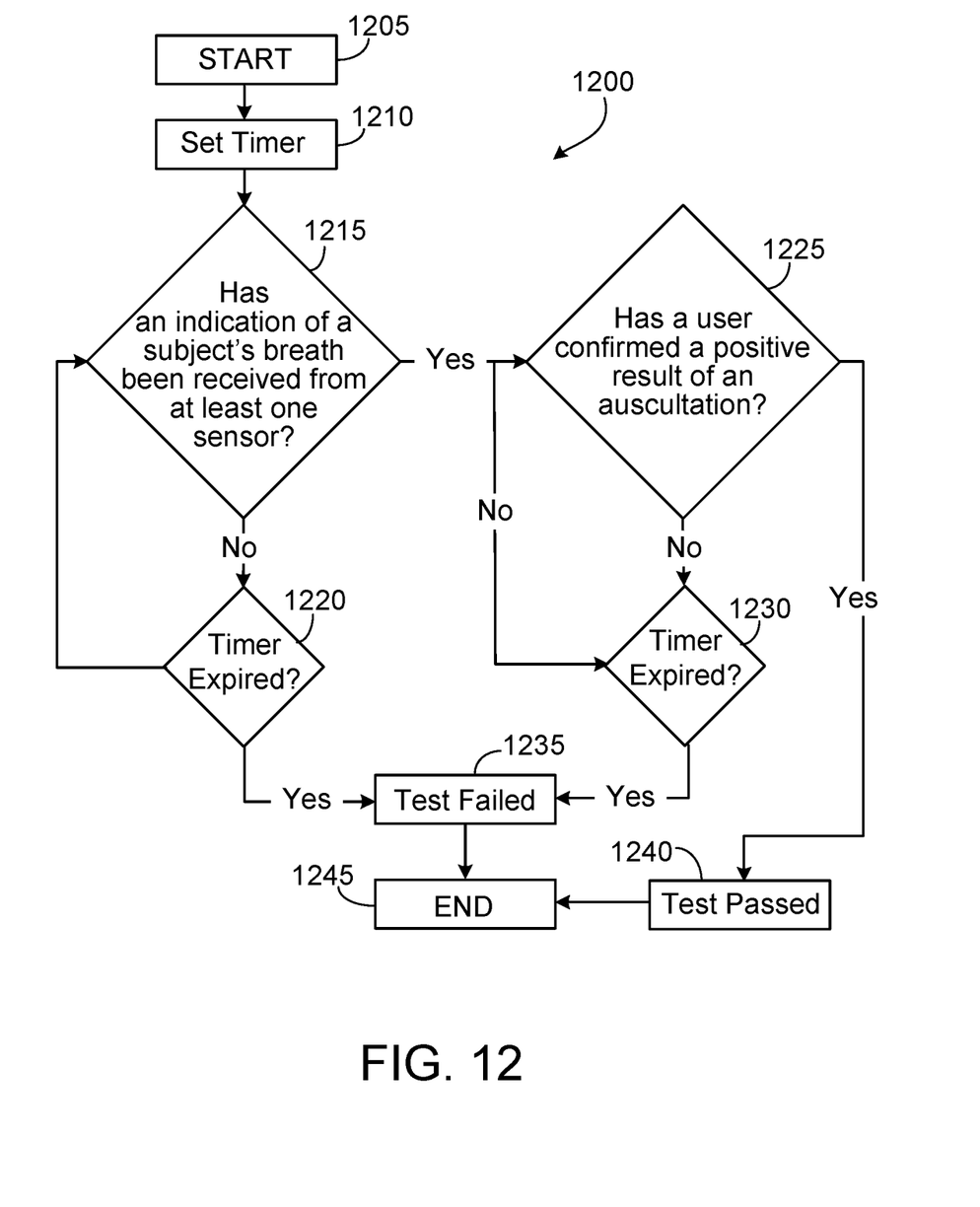
FIG. 12 is a flow diagram depicting a method according to an example embodiment of the invention.

FIG. 12 is a flow diagram depicting a method 1200 according to an example embodiment of the invention. Method 1200 begins at 1205. At 1210, a timer is set. In an embodiment, the timer is a programmable timer such as programmable timer 255 of FIG. 2. In the embodiment, the timer may be set to expire in a range between 30 and 90 seconds, however, other time periods are possible.

At 1215, a determination is made whether an indication of a subject's breath has been received from at least one sensor. The determination may be made by a computer or medical monitor such as system 200 of FIG. 2 configured with a capnography sensor such as capnographic sensor 120 of FIG. 1 or by determining a transthoracic impedance of the subject using, for example, electrodes 135*a* and 135*b* of FIG. 1 configured with system 200. In some embodiments, system 200 may require indications of a subject's breath to be received from both the capnography sensor and electrodes 135*a* and 135*b* for the determination of the subject's breath to be made. In other embodiments, an indication of the subject's breath from one sensor only is necessary for system 200 to make the determination.

At 1215, if an indication of a subject's breath has not been received, then the flow proceeds to 1220. At 1220, if the timer has expired then the test has failed as indicated at 1235. At 1220, if the timer has not expired, then flow proceeds back to 1215.

At 1215, if an indication of a subject's breath has been received, then flow proceeds to 1225. At 1225, a determination is made whether a user has confirmed a positive result of an auscultation of the subject. For example, a user may auscultate a subject's left lung, right lung, left axillary or right axillary listening for an indication of the subject's breath. If a breath sound is heard during these auscultations, the subject's tracheal tube may be inserted correctly and the user may at this point confirm a positive result of the auscultation using system 200, for example. If the user auscultates a subject's abdomen, then a positive result of the auscultation would be that no breath sounds are heard in the abdomen. Hearing breath sounds during auscultation of the abdomen may indicate that the tracheal tube has been inserted incorrectly, for example, into the subject's esophagus. If a positive result of an auscultation has not been confirmed, flow proceeds to 1230.

At 1230, if the timer has expired then the test has failed as indicated at 1235. At 1230, if the timer has not expired, then flow proceeds back to 1225. At 1225, if an indication of a subject's breath has been received, then the test has passed as indicated at 1240 and the test ends at 1245.

Without in any way limiting the scope, interpretation, or application of the claims appearing below, a technical effect of one or more of the example embodiments disclosed herein is to provide a system for monitoring ventilation of a subject and determining whether a tracheal tube such as an endotracheal tube has been properly inserted in a subject's trachea. Embodiments of the present invention may be implemented in software, firmware, hardware, application logic or a combination of software, hardware and application logic. The software, firmware, application logic and/or hardware may reside on at least one system such as system 200 of FIG. 2. In an embodiment, the application logic, software or an instruction set is maintained on any one of various conventional computer-readable media. In the context of this document, a "computer-readable medium" may be any media or means that can contain, store, communicate, propagate or transport the instructions for use by or in connection with an instruction execution system, apparatus, or device, such as a computer, with one example of a computer, system 200, described and depicted in FIG. 2. A computer-readable medium may comprise a computer-readable storage medium that may be any media or means that can contain or store the instructions for use by or in connection with an instruction execution system, apparatus, or device, such as in system 200 of FIG. 2.

If desired, the different functions discussed herein may be performed in a different order and/or concurrently with each other. Furthermore, if desired, one or more of the above-described functions may be optional or may be combined.

Although various aspects of the invention are set out in the independent claims, other aspects of the invention comprise other combinations of features from the described embodiments and/or the dependent claims with the features of the independent claims, and not solely the combinations explicitly set out in the claims.

It is also noted herein that while the above describes example embodiments of the invention, these descriptions should not be viewed in a limiting sense. Rather, there are several variations and modifications which may be made without departing from the scope of the present invention as defined in the appended claims.

What is claimed is:

1. A ventilation monitoring system for assisting in proper placement of an endotracheal tube in a subject, comprising:
    at least one capnography sensor configured to be placed in fluid communication with the endotracheal tube and to provide information representative of the subject's breath; and
    at least one processor in communication with the at least one capnography sensor, the processor configured to:
        within a first predetermined time period for completing a first test, identify at least one first indication of the subject's breath during the first predetermined time period based on the information representative of the subject's breath from the at least one capnography sensor, and identify a positive result of a first auscultation, wherein the first auscultation comprises auscultation of one of a left lung, right lung, left axillary region, right axillary region, or abdomen;
        within a second predetermined time period for completing a second test, identify at least one second indication of the subject's breath during the second predetermined time period based on the information representative of the subject's breath from the at least one capnography sensor, and identify a positive result of a second auscultation, wherein the second auscultation comprises auscultation of another of the left lung, right lung, left axillary region, right axillary region, or abdomen, different from the first auscultation, and wherein the second predetermined time period is after the first predetermined time period; and
        provide an indication of proper endotracheal tube placement when (1) the at least one first indication of the subject's breath and the positive result of the first auscultation are identified within the first predetermined time period, and (2) the at least one second indication of the subject's breath and the positive result of the second auscultation are identified within the second predetermined time period.

2. The ventilation monitoring system of claim 1, further comprising a display coupled with the at least one processor, wherein the indication of proper endotracheal tube placement comprises a visual confirmation of proper endotracheal tube placement provided on the display.

3. The ventilation monitoring system of claim 1, wherein the at least one capnography sensor is configured to measure a concentration or partial pressure of carbon dioxide in respiratory gases of the subject.

4. The ventilation monitoring system of claim 1, wherein the information received from the at least one capnography sensor comprises at least one of carbon dioxide ($CO_2$) concentration, end-tidal $CO_2$, inspired $CO_2$, and respiratory rate of the subject.

5. The ventilation monitoring system of claim 1, wherein the at least one capnography sensor is connected to the at least one processor via a wireless communication channel.

6. The ventilation monitoring system of claim 1, wherein the at least one capnography sensor is connected to the at least one processor via a cable.

7. The ventilation monitoring system of claim 1, wherein the at least one processor is further configured to provide a first prompt via a user interface upon expiration of the first predetermined time period when the at least one first indication of the subject's breath and the positive result of the first auscultation are not identified within the first predetermined time period.

8. The ventilation monitoring system of claim 7, wherein the at least one processor is further configured to provide a second prompt via the user interface upon expiration of the second predetermined time period when the at least one second indication of the subject's breath and the positive result of the second auscultation are not identified within the second predetermined time period.

9. The ventilation monitoring system of claim 1, wherein the first auscultation and/or the second auscultation comprise manual auscultation of one of the left lung, right lung, left axillary region, right axillary region, or abdomen of the subject.

10. The ventilation monitoring system of claim 1, further comprising at least one acoustic sensor in communication with the at least one processor configured to measure breath sounds of the subject, wherein the first auscultation and/or the second auscultation comprise identification of breath sounds for one of the left lung, right lung, left axillary region, right axillary region, or abdomen of the subject based, at least in part, on acoustic information received from the at least one acoustic sensor.

11. The ventilation monitoring system of claim 1, wherein the at least one processor is further configured to provide a notification via a user interface when the first predetermined time period expires before the at least one first indication of the subject's breath and the positive result of the first auscultation are identified and/or to provide a notification via the user interface when the second predetermined time period for completing the second test expires before the at least one second indication of the subject's breath and the positive result of the second auscultation are identified.

12. The ventilation monitoring system of claim 1, further comprising a timer for monitoring the first predetermined time period and the second predetermined time period, wherein the at least one processor is configured to initiate the timer to measure the first predetermined time period after the endotracheal tube is positioned in the subject's trachea, and to initiate the timer to measure the second predetermined time period after the at least one first indication of the subject's breath and the indication of the positive result of the first auscultation are identified by the processor.

13. The ventilation monitoring system of claim 1, further comprising at least two electrodes configured to be positioned on opposing sides of a thoracic cavity of the subject to measure a transthoracic impedance of the subject.

14. The ventilation monitoring system of claim 13, wherein the at least one processor is in communication with the at least two electrodes and is configured to identify the at least one first indication of the subject's breath during the first predetermined time period based on the transthoracic impedance from the at least two electrodes.

15. The ventilation monitoring system of claim 14, wherein the at least one processor is configured to identify the at least one second indication of the subject's breath during the second predetermined time period based on the transthoracic impedance from the at least two electrodes.

16. The ventilation monitoring system of claim 13, wherein the at least one processor is in communication with the at least two electrodes and is configured to identify the at least one first indication of the subject's breath during the first predetermined time period based on signals from both the at least one capnography sensor and the at least two electrodes.

17. The ventilation monitoring system of claim 16, wherein the at least one processor is configured to identify the at least one second indication of the subject's breath during the second predetermined time period based on signals from both the at least one capnography sensor and the at least two electrodes.

18. The ventilation monitoring system of claim 1, further comprising the endotracheal tube configured to be positioned in the subject's trachea.

19. The ventilation monitoring system of claim 1, further comprising a defibrillation unit in communication with the at least one processor.

20. A method for indicating that a subject's endotracheal tube is properly placed performed by at least one processor of a ventilation monitoring system, the method comprising:
within a first predetermined time period for completing a first test, identifying, with the at least one processor, at least one first indication of the subject's breath during the first predetermined time period based on information received from at least one capnography sensor in fluid communication with the subject's endotracheal tube, and identifying, with the at least one processor, a positive result of a first auscultation based on an acoustic signal or user input received by the at least one processor, wherein the first auscultation comprises auscultation of one of a left lung, right lung, left axillary region, right axillary region, and abdomen;
within a second predetermined time period for completing a second test, identifying, with the at least one processor, at least one second indication of the subject's breath during the second predetermined time period based on the received information from the at least one capnography sensor, and identifying, with the at least one processor, a positive result of a second auscultation based on the acoustic signal or the user input received by the at least one processor, wherein the second auscultation comprises auscultation of another of the left lung, right lung, left axillary region, right axillary region, or abdomen, wherein the second predetermined time period is after the first predetermined time period; and
providing by a user interface of the ventilation monitoring system, an indication of proper placement of the endotracheal tube when
(1) the at least one first indication of the subject's breath and the positive result of the first auscultation are identified within the first predetermined time period, and
(2) the at least one second indication of the subject's breath and the positive result of the second auscultation are identified within the second predetermined time period.

21. The method of claim 20, wherein providing the indication of proper tube placement comprises displaying a visual indication of proper tube placement on a display in electronic communication with the processor of the ventilation monitoring system.

22. The method of claim 20, wherein the at least one capnography sensor is configured to measure a partial pressure of carbon dioxide in respiratory gases of the subject.

23. The method of claim 20, wherein the information received from the at least one capnography sensor comprises at least one of carbon dioxide ($CO_2$) concentration, end-tidal $CO_2$, inspired $CO_2$, or respiratory rate of the subject.

24. The method of claim 20, further comprising providing a notification via the user interface upon expiration of the first predetermined time period when the first indication of the subject's breath or the positive result of the first auscultation are not identified within the first time period, and providing a notification via the user interface upon expiration of the second predetermined time period when the second indication of the subject's breath or the positive result of the second auscultation are not identified within the second time period.

25. The method of claim 20, wherein the acoustic signal is received from at least one acoustic sensor configured to measure breath sounds of the subject.

26. The method of claim 20, wherein the first auscultation and/or the second auscultation comprise manual auscultation of the left lung, right lung, left axillary region, right axillary region, or abdomen of the subject.

27. The method of claim 20, further comprising automatically measuring the first predetermined time period and/or the second predetermined time period with a timer associated with the processor of the ventilation monitoring system.

28. The method of claim 20, further comprising, once the endotracheal tube is believed to be positioned at a predetermined position in the trachea of the subject, initiating a timer of the ventilation monitoring system to measure the first predetermined time period and, after the at least one indication of the subject's breath and the positive result of the first auscultation are identified by the processor, initiating the timer to measure the second predetermined time period.

29. The method of claim 20, wherein identifying the at least one first indication of the subject's breath during the first predetermined time period is based, at least in part, on information representative of a transthoracic impedance of the subject received from at least two electrodes positioned on opposing sides of a thoracic cavity of the subject.

30. The method of claim 29, wherein identifying the at least one first indication of the subject's breath during the first predetermined time period is based on signals received by the at least one processor from both the at least one capnography sensor and the at least two electrodes.

31. The method of claim 20, wherein identifying the at least one second indication of the subject's breath during the second predetermined time period is based, at least in part, on information representative of a transthoracic impedance of the subject received from at least two electrodes positioned on opposing sides of a thoracic cavity of the subject.

32. The method of claim 31, wherein identifying the at least one first indication of the subject's breath during the first predetermined time period is based on signals received by the at least one processor from both the at least one capnography sensor and the at least two electrodes.

\* \* \* \* \*